United States Patent
Ryu et al.

(10) Patent No.: US 9,421,381 B2
(45) Date of Patent: Aug. 23, 2016

(54) SYSTEMS AND METHODS FOR OPTIMIZING MULTI-SITE LEFT VENTRICULAR PACING BASED ON INTERELECTRODE CONDUCTION DELAYS

(75) Inventors: Kyungmoo Ryu, Palmdale, CA (US); Stuart Rosenberg, Castaic, CA (US); Allen Keel, San Francisco, CA (US)

(73) Assignee: Paceseter, Inc., Sylmar, CA (US)

( * ) Notice: Subject to any disclaimer, the term of this patent is extended or adjusted under 35 U.S.C. 154(b) by 1983 days.

(21) Appl. No.: 12/607,817

(22) Filed: Oct. 28, 2009

(65) Prior Publication Data

US 2011/0098770 A1  Apr. 28, 2011

(51) Int. Cl.
*A61N 1/368* (2006.01)
*A61N 1/362* (2006.01)

(52) U.S. Cl.
CPC .............. *A61N 1/3627* (2013.01); *A61N 1/368* (2013.01); *A61N 1/3684* (2013.01)

(58) Field of Classification Search
USPC ........... 607/1–2, 9, 11, 14–15, 17, 25, 27, 29, 607/36, 37, 115, 116, 119, 123
See application file for complete search history.

(56) References Cited

U.S. PATENT DOCUMENTS

| | | | |
|---|---|---|---|
| 7,139,609 B1 | 11/2006 | Min et al. | |
| 7,248,925 B2 | 7/2007 | Bruhns et al. | |
| 7,440,804 B1 | 10/2008 | Min et al. | |
| 2006/0155338 A1* | 7/2006 | Mongeon et al. | 607/9 |
| 2008/0097536 A1* | 4/2008 | Kramer et al. | 607/9 |
| 2008/0262361 A1 | 10/2008 | Gutfinger et al. | |

* cited by examiner

*Primary Examiner* — Deborah Malamud

(57) ABSTRACT

Techniques are provided for use with an implantable cardiac stimulation device equipped for multi-site left ventricular (MSLV) pacing using a multi-pole LV lead. In one example, MSLV interelectrode conduction delays are determined among the electrodes of the multi-pole LV lead. MSLV interelectrode pacing delays are then set based on the MSLV interelectrode conduction delays for use in delivering MSLV pacing. To this end, various criteria are exploited for determining optimal values for the pacing delays based on the interelectrode conduction delays. MSLV pacing is then controlled using the specified MSLV interelectrode pacing delays. In some examples, the optimization procedure is performed by the implantable device itself. In other examples, the procedure is performed by an external programmer device. In such an embodiment, the external device determines optimal MSLV interelectrode pacing delays and then transmits programming commands to the implantable device to program the device to use the pacing delays.

23 Claims, 11 Drawing Sheets

```
          ┌─────────────────────┐
          │  PACING EFFICACY    │
          │  CONSIDERATIONS     │
          └─────────────────────┘
                    │                          214
                    ▼
┌──────────────────────────────────────────────────┐
│ DELIVER A SET OF MSLV TEST PACING PULSES USING   │
│ SELECTED PERMUTATIONS OF LV PACING VECTORS, SUCH │
│ AS VECTORS CHOSEN FROM:                          │
│                                                  │
│ LV TIP – RV COIL; LV RING1 – RV COIL; LV RING2 – │
│ RV COIL; LV RING3 – RV COIL; LV TIP – LV RING1;  │
│ LV TIP – LV RING3; LV RING 1 – LV RING3; LV RING2 – │
│ LV RING1; LV RING2 – LV RNG3; LV RING3 – LV RING1 │
└──────────────────────────────────────────────────┘
                    │                          216
                    ▼
┌──────────────────────────────────────────────────┐
│ DETECT PARAMETERS REPRESENTATIVE OF CARDIAC      │
│ PACING EFFICACY FOR EACH PERMUTATION INCLUDING   │
│ ONE OR MORE OF:                                  │
│                                                  │
│ – QUICKEST ACTIVATION TIME TO NON-PACED SITES IN │
│   THE LV OR RV                                   │
│ – SHORTEST QRS DURATION (AT NON-PACED SITES IN   │
│   THE LV OR RV)                                  │
│ – LEAST DEGREE OF LV OR RV IEGM FRACTIONATION    │
│ – BEST HEMODYNAMIC RESPONSE (AS DETECTED BY THE  │
│   IMPLANTED DEVICE OR BY AN EXTERNAL DEVICE)     │
└──────────────────────────────────────────────────┘
                    │                          218
                    ▼
┌──────────────────────────────────────────────────┐
│ IDENTIFY AND SELECT PARTICULAR PERMUTATIONS THAT │
│       YIELD THE GREATEST PACING EFFICACY         │
└──────────────────────────────────────────────────┘
```

FIG. 5

ALTERNATIVE CRITERIA FOR USE WITH SINGLE-SITE LV PACING

250

FOR SINGLE-SITE PACING WHEN USING A MULTI-POLE LV LEAD SELECT THE LV PACING SITE BASED ON ONE OR MORE OF:

- PACING SITE AND PACING VECTOR THAT YIELDS NO SIGNIFICANT PHRENIC NERVE STIMULATION
- PACING SITE AND PACING VECTOR THAT YIELDS THE LOWEST PACING CAPTURE THRESHOLD
- PACING SITE THAT YIELDS THE LARGEST AMPLITUDE OF SENSED ELECTROGRAM
- PACING SITE THAT YIELDS THE SHORTEST ACTIVATION TO THE RV SENSED CHANNEL AFTER TESTING ALL PACING VECTORS AT EACH LV SITE
- PACING SITE THAT YIELDS THE SHORTEST ACTIVATION TO THE REST OF LV SENSED CHANNELS AFTER TESTING ALL PACING VECTORS AT EACH LV SITE
- PACING SITE THAT YIELDS MINIMUM VARIABILITY IN INTERELECTRODE TIMING DELAYS BETWEEN LV ELECTRODES WHEN PACED AT EACH LV SITE
- PACING SITE THAT YIELDS NO FRACTIONATION (OR LESS FRACTIONATED) ELECTROGRAMS DETECTED ON THE REST OF LV SENSED CHANNELS
- PACING SITE THAT YIELDS SEQUENTIAL ACTIVATION, NO MULTIDIRECTIONAL ACTIVATION DETECTED ON THE REST OF LV SENSED CHANNELS
- PACING SITE THAT YIELDS OPTIMAL HEMODYNAMIC RESPONSE (E.G., CARDIOGENIC IMPEDANCE, LEFT ATRIAL PRESSURE) AS MEASURED BY THE DEVICE OR AN EXTERNAL SYSTEM
- PACING SITE THAT YIELDS NO PROARRHYTHMIC EVENTS

FIG. 7

ALTERNATIVE CRITERIA FOR USE WITH MULTI-SITE LV PACING

252

FOR MULTI-SITE PACING WHEN USING A MULTI-POLE LV LEAD WITHOUT INTERELECTRODE PACING DELAYS, SELECT PACING VECTOR PERMUTATIONS BASED ON ONE OR MORE OF:

- THE PERMUTATION THAT YIELDS NO SIGNIFICANT PHRENIC NERVE STIMULATION
- THE PERMUTATION THAT YIELDS LOWEST COMBINED PACING CAPTURE THRESHOLD
- THE PERMUTATION THAT HAS HIGHEST COMBINED SENSED ELECTROGRAM AMPLITUDE
- THE PERMUTATION THAT YIELDS THE SHORTEST ACTIVATION TO THE RV SENSED CHANNEL
- THE PERMUTATION THAT YIELDS OPTIMAL HEMODYNAMIC RESPONSE (E.G., CARDIOGENIC IMPEDANCE, LEFT ATRIAL PRESSURE) AS MEASURED BY THE DEVICE OR AN EXTERNAL SYSTEM
- THE PERMUTATION THAT YIELDS NO FRACTIONATION (OR LESS FRACTIONATION) OF ELECTROGRAM AT NON-PACED SITES
- THE PERMUTATION THAT YIELDS THE QUICKEST ACTIVATION TO NON-PACED SITES
- THE PERMUTATION THAT PRODUCES NO PROARRHYTHMIC EVENTS

FIG. 8

SYSTEMS AND METHODS FOR OPTIMIZING MULTI-SITE LEFT VENTRICULAR PACING BASED ON INTERELECTRODE CONDUCTION DELAYS

FIELD OF THE INVENTION

The invention generally relates to implantable cardiac stimulation devices such as pacemakers, implantable cardioverter-defibrillators (ICDs) and cardiac resynchronization therapy (CRT) devices and, in particular, to techniques for optimizing and controlling multi-site left ventricular (LV) pacing for use with devices equipped with multi-pole LV leads.

BACKGROUND OF THE INVENTION

Some implantable cardiac stimulation devices are equipped with multi-pole LV leads, i.e. leads provided with a set of electrodes sufficient to permit multi-site LV (MSLV) pacing. For such devices, it is desirable to determine optimal MSLV interelectrode pacing delays for use in delivering MSLV pacing. The MSLV interelectrode pacing delays can, for example, specify time delays between delivery of electrical pacing pulses at different sites within the LV or along different pacing vectors. The MSLV pulses may be coordinated with the delivery of pulses to the RV via a bipolar RV lead so as to improve cardiac hemodynamics. In particular, MSLV pacing may be coordinated with RV pacing to provide CRT pacing, which seeks to normalize asynchronous cardiac electrical activation and resultant asynchronous contractions associated with congestive heart failure (CHF) by delivering synchronized pacing stimulus to both ventricles. The RV and MSLV stimulus are synchronized so as to improve overall cardiac function. This may have the additional beneficial effect of reducing the susceptibility to life-threatening tachyarrhythmias.

Accordingly, some aspects of the invention are directed to providing systems and methods for determining preferred or optimal MSLV interelectrode pacing delays for use with MSLV pacing, particularly MSLV CRT. Other some aspects of the invention are directed to determining preferred or optimal combinations of LV electrodes or permutations of MSLV pacing vectors for use in delivering MSLV pacing using a multi-pole LV lead.

SUMMARY OF THE INVENTION

In an exemplary embodiment, a method is provided for use with an implantable cardiac stimulation device equipped for MSLV pacing using a multi-pole LV lead. In one example, MSLV interelectrode conduction delays are determined among a plurality of electrodes of the multi-pole LV lead. MSLV interelectrode pacing delays are then set based on the MSLV interelectrode conduction delays for use in delivering MSLV pacing using the multi-pole LV lead. MSLV pacing is then controlled using the MSLV interelectrode pacing delays. In some examples, the method is performed by the implantable device itself. In other examples, at least some of the steps are performed by an external programmer device. In such an embodiment, the external device determines the MSLV interelectrode pacing delays and then transmits programming commands to the implantable device to program the device to use the MSLV interelectrode pacing delays.

In an illustrative implementation of the invention where the device itself performs the steps of the method, various factors are employed by the device to determine preferred or optimal MSLV interelectrode pacing delays. For example, the device measures or otherwise determines MSLV interelectrode conduction delays during one or more of: single-site LV pacing, single-site RV pacing, and sinus rhythm. The device then sets the MSLV interelectrode pacing delays (up to a maximum of, e.g., 80 milliseconds (ms)) based on the measured conduction delays using one or more of the following considerations: the interelectrode pacing delays are set to values programmed in the range of 5-95% of the corresponding conduction delay detected during single-site LV pacing; the interelectrode pacing delays are set to values less than or equal to the corresponding conduction delay detected during single-site RV pacing; the interelectrode pacing delays are set to values in a $\pm X$ % range around the corresponding conduction delay values detected during single-site RV pacing (where X is a programmable value); the interelectrode pacing delays are set to values less than or equal to the corresponding conduction delay detected during sinus rhythm; or the interelectrode pacing delays are set to values in a $\pm Y$ % range around corresponding conduction delays detected during sinus rhythm (where Y is also programmable value). Also, preferably, the device rejects any MSLV interelectrode pacing delays that produce adverse cardiac pacing effects. Adverse cardiac pacing effects can include proarrhythmic effects, irregular activation at non-paced sites in the LV, and/or irregular activation at non-paced sites in the right ventricle (RV).

In the illustrative implementation, the implantable device also identifies preferred or optimal pacing vectors (or permutations of pacing vectors) for use in delivering the MSLV pacing. For example, the device detects or otherwise obtains one or more parameters representative of cardiac pacing efficacy for each permutation of pacing vectors including: QRS durations; hemodynamic response (as detected by the implanted device or by an external device); the degree of LV or RV IEGM fractionation; and/or activation times to non-paced sites in the LV or RV. The particular permutation of pacing vectors that yields the greatest pacing efficacy is identified based on an examination of these parameters and is then activated for delivering MSLV pacing.

In some examples, the device is programmed to deliver a series of test pacing pulses using each permutation of pacing vectors, wherein the test pacing pulses are delivered throughout a range of different MSLV interelectrode pacing delays (up to, e.g., 80 ms). The device detects the aforementioned parameters for each different MSLV interelectrode pacing delay value and for each permutation of pacing vectors and then determines the particular combination of MSLV interelectrode pacing delay and pacing vector permutation providing the best cardiac pacing efficiency while also avoiding any adverse cardiac effects. This combination is then employed in the actual delivery of MSLV pacing.

It should be understood that, in addition to determining and exploiting preferred or optimal MSLV interelectrode pacing delays, the device can also be equipped to determine preferred or optimal atrioventricular (AV) and interventricular (VV) pacing delays for use in controlling CRT or other pacing therapies.

Although summarized primarily with respect to implementations having a multi-pole LV lead, aspects of the invention are also generally applicable to other multi-pole leads, such as multi-pole RV leads or multi-pole atrial leads. More generally, a method is provided for use with an implantable cardiac stimulation device equipped for multi-site pacing using at least one multi-pole lead. Interelectrode conduction delays are determined among a plurality of electrodes of the multi-pole lead. Interelectrode pacing delays are then set based on the interelectrode conduction delays for use in delivering multi-site pacing using the multi-pole lead. Multi-site pacing is then controlled using the interelectrode pacing delays.

System and method implementations of these and other techniques are presented herein.

BRIEF DESCRIPTION OF THE DRAWINGS

Features and advantages of the described implementations can be more readily understood by reference to the following description taken in conjunction with the accompanying drawings.

FIG. 5 particularly illustrates techniques for assessing pacing efficacy that may be exploited by the implementation of FIG. 3;

FIG. 7 summarizes a set of criteria for use in selecting pacing sites for use with single-site LV pacing;

FIG. 8 summarizes a set of criteria for use in selecting pacing vector permutations for use with MSLV pacing wherein no significant interelectrode pacing delays are applied;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
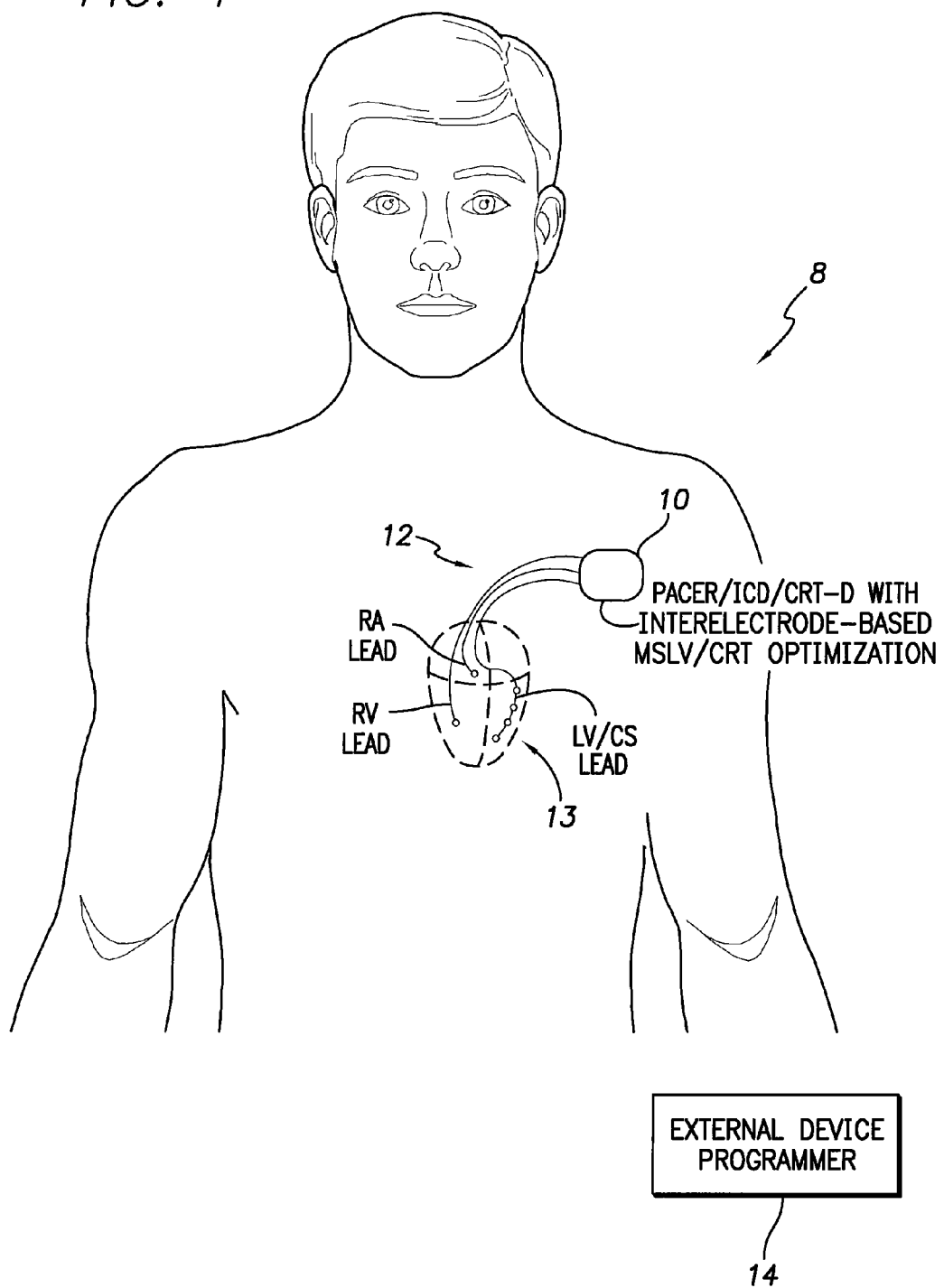
FIG. 1 illustrates pertinent components of an implantable medical system having a pacemaker, ICD or CRT-D device capable of optimizing MSLV interelectrode pacing delays and pacing vector permutations.

FIG. 1 illustrates an implantable medical system 8 capable of optimizing MSLV interelectrode pacing delays and pacing vector permutations. The medical system 8 includes a pacer/ICD 10 or other cardiac stimulation device (such as a CRT-D) equipped with one or more cardiac sensing/pacing leads 12 implanted on or within the heart of the patient, including a multi-pole LV lead implanted via the coronary sinus (CS). In FIG. 1, a stylized representation of leads is provided. To illustrate the multi-pole configuration of the LV lead, a set of electrodes 13 is shown distributed along the LV lead. The RV and RA leads are each shown with a single electrode, though each of those leads may include additional electrodes as well, such as bipolar tip/ring electrode pairs, shocking coils, etc. Still further, the LV lead can also include one or more left atrial (LA) electrodes mounted on or in the LA via the CS, as well as additional shocking coils. See FIG. 9 for a more complete and accurate illustration of various exemplary leads.

In some implementations, the pacer/ICD itself performs the optimization based on electrocardiac signals sensed using the leads. In other implementations, the device transmits pertinent parameters to an external device programmer 14 that performs the optimization. That is, the device programmer determines the optimal MSLV interelectrode pacing delays and pacing vector permutations for the patient, which are then programmed into the pacer/ICD via telemetry. Other external devices might instead be used to perform the optimization, such as bedside monitors or the like. In some embodiments, the external device is directly networked with a centralized computing system, such as the HouseCall™ system or the Merlin@home/Merlin.Net systems of St. Jude Medical.

In the following illustrative examples, it is assumed that the pacer/ICD performs the optimization using on-board components. An example where the external programmer performs the optimization is described below with reference to FIG. 11.

MSLV Interelectrode-Based Pacing Optimization

Figure 2:
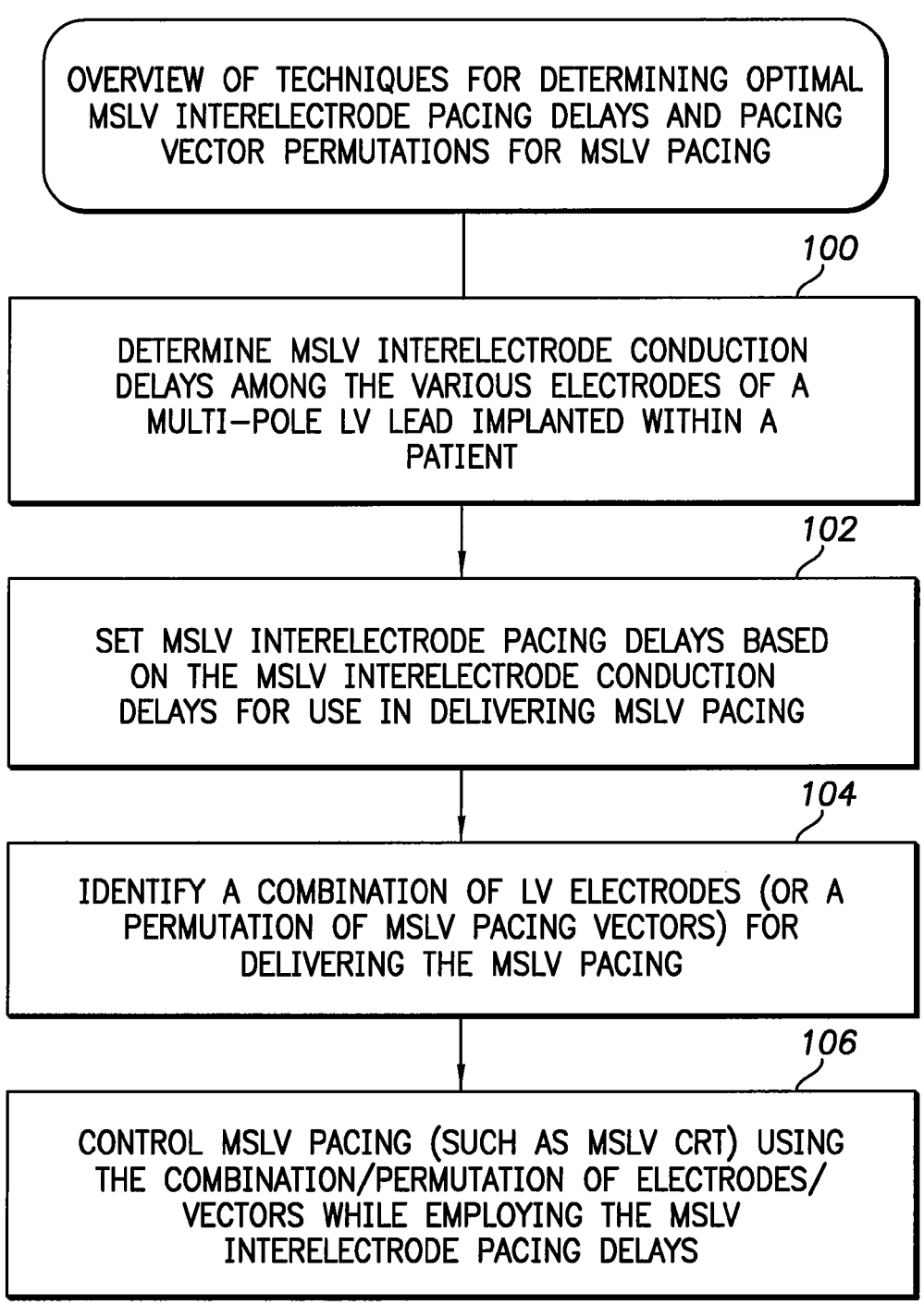
FIG. 2 summarizes a general technique for determining preferred or optimal MSLV interelectrode pacing delays and pacing vector permutations that may be performed by the system of FIG. 1.

FIG. 2 broadly summarizes a general technique that may be exploited by the pacer/ICD of FIG. 1 (or other suitably equipped systems) for determining optimal MSLV interelectrode pacing delays and pacing vector permutations for MSLV pacing. Beginning at step 100, the pacer/ICD determines MSLV interelectrode conduction delays among the various electrodes of a multi-pole LV lead implanted within a patient. For an example where the LV lead is a quadra-pole lead with a tip electrode and three ring electrodes, the device determines interelectrode conduction delays between each pair of LV electrodes (LV tip-LV ring1, LV tip-LV ring2, LV tip-LV ring3, LV ring1-LV ring2, LV ring1-LV ring3, LV ring2-LV ring3) or, at least, between some selectable subset of these pairs. The interelectrode conduction delay generally represents the time delay between detection of electrocardiac events at the different LV electrodes. For example, the conduction delay can represent the time delay between detection of the peak of an intrinsic QRS complex during sinus rhythm at each of the different LV electrodes (as sensed in a unipolar sensing configuration (e.g. tip-case)) or it can represent the time delay between detection of the peak of a paced QRS complex at each of the different LV electrodes (again in unipolar sensing configurations.) The unipolar sensing configuration is just one example. The unipolar sensing configuration is particularly well-suited for use with multi-electrode LV leads having fixed interelectrode distances of about 20-10-17 mm (distal to proximal.) However, a bipolar sensing configuration may be beneficial in multi-electrode LV leads having a tighter interelectrode distance. Exemplary techniques for measuring or detecting various MSLV interelectrode conduction delays are described in greater detail below.

At step 102, the pacer/ICD sets or determines preferred or optimal MSLV interelectrode pacing delays based on the interelectrode conduction delays for use in delivering MSLV pacing. For the example where the LV lead is a quadra-pole lead, the device determines interelectrode pacing delays to be applied between each pacing vector that might be used with the quadra-pole lead. More specifically, for an example where pacing is to be employed in conjunction with an RV lead having an RV coil electrode, the following ten pacing vectors might be selectable by the device for delivering pacing pulses: LV tip-RV coil; LV ring1-RV coil; LV ring2-RV coil; LV ring3-RV coil; LV tip-LV ring1; LV tip-LV ring3; LV ring 1-LV ring3; LV ring2-LV ring1; LV ring2-LV ring3; LV ring3-LV ring1. Note that some of these pacing vectors extend between the RV and LV. Others are entirely within the LV. Nevertheless, the vectors are all considered MSLV pacing vectors since each exploits at least one LV electrode.

The interelectrode pacing delay generally represents the time delay to be employed during MSLV pacing between pulses delivered using different LV pacing vectors. For example, the pacing delay might represent the time delay between a V-pulse delivered using the LV tip-RV coil vector and another V-pulse delivered using the LV ring1-RV coil vector. Hence, separate pacing delays can potentially be determined for use among or between all of the vectors that are selectable by the device (based on its programming and circuitry.) As such, the interelectrode pacing delays generally include intervector pacing delays. (Indeed, as the term is used herein, "interelectrode pacing delay" encompasses intervector pacing delays.) Exemplary techniques for determining or setting the MSLV interelectrode pacing delays based on the MSLV interelectrode conduction delays are described in greater detail below.

Note that, depending upon the capabilities of the device, individual pacing pulses might be delivered using two or more vectors. For example, one pulse might be delivered simultaneously using both the LV tip-RV coil vector and the LV Ring1-RV coil vector. Another pulse might be delivered (subject to a delay) using both the LV Ring2-LV Ring3 vector and the LV Ring3-LV Ring1 vector. A pacing delay value can thereby be specified for use between these two pacing vector permutations. That is, a permutation represents a unique combination of pacing vectors. Hence, in general, the MSLV interelectrode pacing delays determined at step 102 can be determined among or between any selectable permutation of pacing vectors. As can be appreciated, depending upon the number of output pulse channels accommodated by the device and the number of selectable pacing vectors, a large number of permutations might be available and hence a large number of pacing delays can be separately specified. As a practical matter, some subset of the total number of possible permutations can be used, such as permutations limited to only one or two vectors.

At step 104, the device identifies a preferred or optimal combination of LV electrodes (or a permutation of MSLV pacing vectors) for delivering the MSLV pacing. As will be explained, some combinations of LV electrodes (or permutations of pacing vectors) might be rejected as being proarrhythmic or for other reasons. Also, various cardiac pacing efficacy parameters can be measured for use in identifying particular combinations/permutations of electrodes/vectors for use in actually delivering MSLV pacing to achieve advantageous hemodynamic effects. Exemplary techniques exploiting these and other considerations are described in greater detail below.

At step 106, the device controls MSLV pacing using the selected combination/permutation of electrodes/vectors and while employing the MSLV interelectrode pacing delays determined for those electrodes/vectors. Depending upon the implementation, the MSLV pacing delivered at step 106 can be coordinated with RV pacing so as to provide for CRT.

Note that, in addition to determining and using the aforementioned MSLV interelectrode pacing delays, the device can also determine and use various AV/PV pacing delays and VV pacing delays.

The following patents and patent applications set forth various systems and methods for allowing a pacemaker, ICD, CRT device or other cardiac stimulation device to determine and/or adjust AV/PV/VV pacing delays so as to help maintain the pacing delays at optimal values: U.S. patent application Ser. No. 10/703,070, filed Nov. 5, 2003, entitled "Methods for Ventricular Pacing"; U.S. patent application Ser. No. 10/974,123, filed Oct. 26, 2004; U.S. patent application Ser. No. 10/986,273, filed Nov. 10, 2004; U.S. patent application Ser. No. 10/980,140, filed Nov. 1, 2004; U.S. patent application Ser. No. 11/129,540, filed May 13, 2005; U.S. patent application Ser. No. 11/952,743, filed Dec. 7, 2007. See, also, U.S. patent application Ser. No. 12/328,605, filed Dec. 4, 2008, entitled "Systems and Methods for Controlling Ventricular Pacing in Patients with Long Intra-Atrial Conduction Delays", U.S. patent application Ser. No. 12/132,563, filed Jun. 3, 2008, entitled "Systems and Methods for determining Intra-Atrial Conduction Delays using Multi-Pole Left Ventricular Pacing/Sensing Leads", and U.S. patent application Ser. No. 12/507,679, filed Jul. 22, 2009, entitled "Systems and Methods for Optimizing Ventricular Pacing Delays During Atrial Fibrillation." See, further, U.S. Pat. No. 7,248,925, to Bruhns et al., entitled "System and Method for Determining Optimal Atrioventricular Delay based on Intrinsic Conduction Delays." At least some of the techniques are implemented within the QuickOpt™ systems of St. Jude Medical.

In particular, techniques are set forth within at least some of these patent documents for exploiting various inter-atrial and interventricular conduction delays to determine preferred or optimal AV/PV/VV pacing delays. Techniques are also set forth for exploiting the VV delays to determine which ventricles should be paced—the left ventricle (LV), the right ventricle (RV), both ventricles, or neither, and in which order.

Note also that, in the examples described herein, the multi-pole ventricular lead is an LV lead, but it should be understood that aspects of the invention are applicable to multi-pole RV leads. Indeed, at least some of the techniques described herein are also generally applicable to implementations wherein both the LV and RV have multi-pole leads. Still further, the techniques might be applicable to multi-pole atrial leads, implanted on or in either the RA or the LA. As such, at least some of the techniques described herein are generally applicable to optimizing various interelectrode pacing delays/permutations as applied leads implanted on or in any of the four chambers of the heart.

Thus, FIG. 2 summarizes a broad technique for determining optimal MSLV interelectrode pacing delays and pacing vector permutations. It should be understood that the optimal delays/permutations are not necessarily absolutely optimal in a given quantifiable or mathematical sense. As can be appreciated, what constitutes an "optimal" pacing delay or pacing vector permutation depends on the criteria used for judging the resulting pacing performance, which can be subjective in the minds of some clinicians. The pacing delays/permutations determined herein represent, at least, "preferred" pacing delays and/or vector permutations. Clinicians may choose to adjust or alter the selection via device programming for particular patients, at their discretion.

Exemplary MSLV Optimization Techniques

Turning now to FIGS. 3-6, various exemplary MSLV optimization techniques will now be described that serve to determine preferred or optimal MSLV interelectrode pacing delays and/or combinations/permutations of electrodes/vectors. In these examples, the pacer/ICD performs the various optimization steps. It should be understood that at least some of the steps could instead be performed by external devices.

Figure 3:
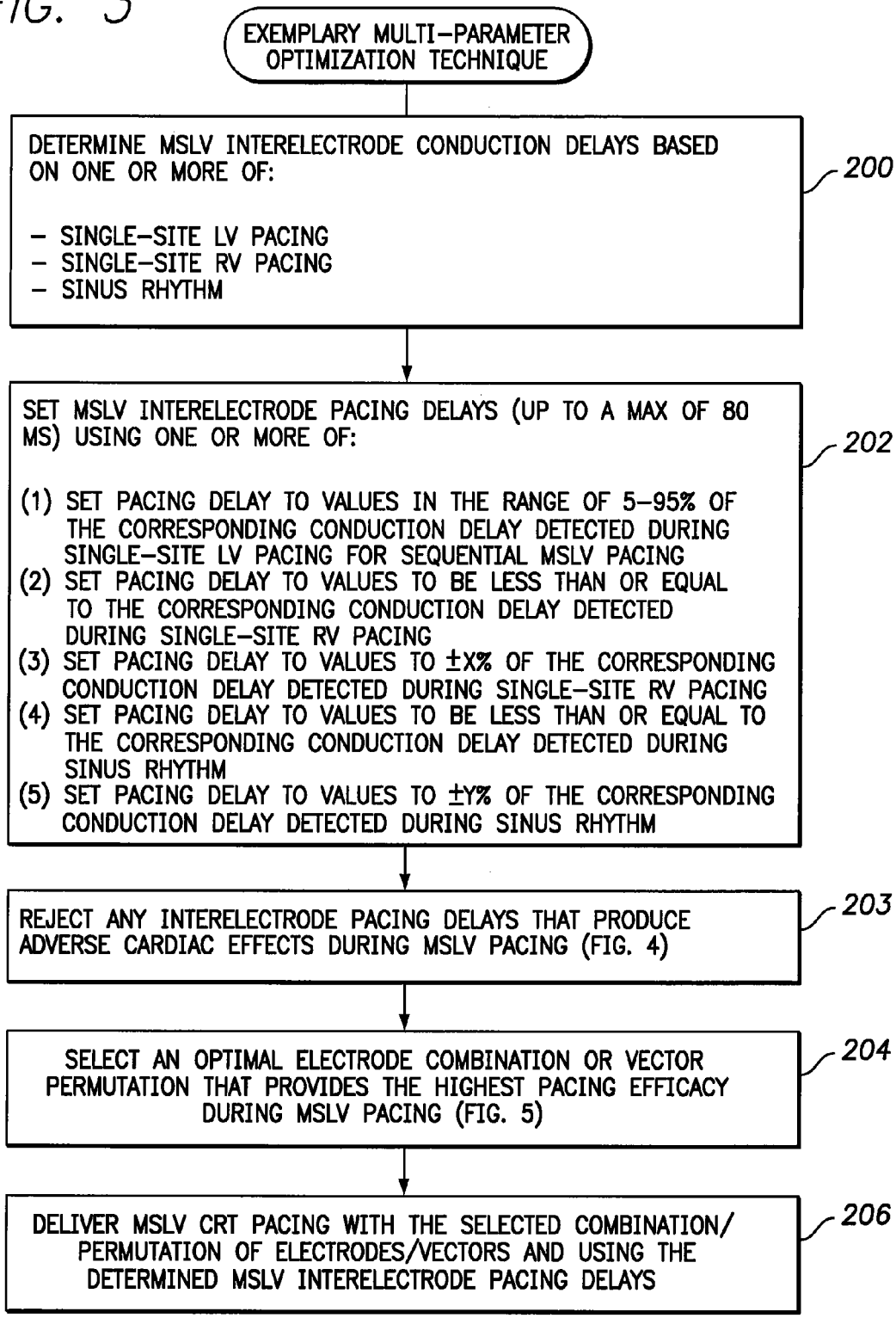
FIG. 3 is a flowchart illustrating an exemplary implementation of the technique of FIG. 2 wherein multiple parameters are measured or detected to optimize MSLV interelectrode pacing delays and pacing vector permutations.

Beginning with step 200 of FIG. 3, the pacer/ICD determines MSLV interelectrode conduction delays based on one or more of: single-site LV pacing, single-site RV pacing; and sinus rhythm. For the example of single-site LV pacing, the device can deliver a set of V-pulses in a unipolar configuration using the LV tip electrode (i.e. LV tip-case) while measuring LV interelectrode conduction delays based on the paced QRS events triggered in the LV by the test pulses. (These events might also be referred to as Evoked Responses.) For a quadra-pole example, the device can measure the LV tip-LV ring1 delay based on the time delay from the V-pulse to the peak of the paced QRS as detected using LV ring1 (in a unipolar sensing configuration.) The device can measure the LV ring1-LV ring2 delay based on the time delay from the peak of the paced QRS as detected using LV ring1 to the peak of the paced QRS as detected using LV ring2; and so on to determine an interelectrode conduction delay for each unique pair of LV electrodes.

For the example of single-site RV pacing, the device can, e.g., deliver a set of V-pulses in a bipolar configuration using the RV tip and ring electrodes (i.e. RV tip-RV ring) while measuring LV interelectrode conduction delays based on the paced QRS events triggered in the LV by the test pulses. For the quadra-pole example, the device can measure the LV tip-LV ring1 delay based on the time delay from the peak of the paced QRS as detected using the LV tip (in a unipolar sensing configuration) to the from the peak of the paced QRS as detected using the LV ring1 (also in a unipolar sensing configuration.) The device can measure the LV ring1-LV ring2 delay based on the time delay from the peak of the paced QRS as detected using LV ring1 to the peak of the paced QRS as detected using LV ring2; and so on to determine an interelectrode conduction delay for each unique pair of LV electrodes.

For the example of sinus rhythm, the device detects sinus rhythm using otherwise conventional techniques and then measures LV interelectrode conduction delays based on the intrinsic QRS events occurring during sinus rhythm. For the quadra-pole example, the device can measure the LV tip-LV ring1 delay based on the time delay from the peak of the intrinsic QRS as detected using the LV tip to the from peak of the intrinsic QRS as detected using the LV ring1. The device can measure the LV ring1-LV ring2 delay based on the time delay from the peak of the intrinsic QRS as detected using LV ring1 to the peak of the paced QRS as detected using LV ring2; and so on to determine an interelectrode conduction delay for each unique pair of LV electrodes.

At step 202, the device then sets or determines the MSLV interelectrode pacing delays (up to a max of, e.g., 80 ms) using one or more of the following criteria (which depend, in part, on the manner by which the interelectrode conduction delays were determined at step 200):

(1) set pacing delay to values in the range of 5-95% of the corresponding conduction delay detected during single-site LV pacing for sequential MSLV pacing (2) set pacing delay to values to be less than or equal to the corresponding conduction delay detected during single-site RV pacing (3) set pacing delay to values to ±X % of the corresponding conduction delay detected during single-site RV pacing (4) set pacing delay to values to be less than or equal to the corresponding conduction delay detected during sinus rhythm (5) set pacing delay to values to ±Y % of the corresponding conduction delay detected during sinus rhythm.

Regarding procedure (1), the device may be programmed with a scaling value in the range of 5%-95%. The device then applies that scaling value to the LV interelectrode delays (obtained during single-site LV pacing) to set the corresponding LV interelectrode pacing delays for any pacing vector that employs those same electrodes. Consider a first example where the device is programmed to sequentially deliver pacing pulses using the following "cross-chamber" vectors: LV tip-RV coil; LV Ring1-RV coil; LV Ring2-RV coil; LV Ring3-RV coil. To determine the pacing delay between the LV tip-RV coil vector and the LV Ring1-RV coil vector, the device applies the scaling factor to the LV tip-LV ring1 conduction delay to set the pacing delay. To determine the pacing delay between the LV ring1-RV coil vector and the LV Ring2-RV coil vector, the device applies the same scaling factor to the LV ring1-LV ring2 conduction delay; and so on. Consider a second example where the device is instead programmed to sequentially deliver pacing pulses using the following "intraventricular" vectors: LV tip-LV ring1; LV ring1-LV ring2; LV ring2-LV ring3. To determine the pacing delay between the LV tip-LV ring1 vector and the LV ring1-LV ring2 vector, the device applies the scaling factor to the LV tip-LV ring1 conduction delay to set the pacing delay. To determine the pacing delay between the LV ring1-LV ring2 vector and the LV ring2-LV ring3 vector, the device applies the same scaling factor to the LV ring1-LV ring2 conduction delay; and so on.

In this manner, using procedure (1), the device sets pacing delays between pairs of pacing vectors based on the corresponding interelectrode conduction delays using the scaling factor. That is, for any given pair of pacing vectors, the device identifies a corresponding interelectrode conduction delay—based the particular LV electrodes of the vectors—and then applies the scaling factor to that conduction delay to set the pacing delay. Otherwise routine experimentation can be employed in advance to determine a preferred or optimal value for the scaling factor (within the range of 5-95%). This may be achieved by assessing the relative hemodynamic efficacy of various different scaling factors in clinical settings. The preferred scaling factor is then programmed into the device for use with the patient, subject to clinician review.

Thus, interelectrode conduction delays are used to set interelectrode (i.e. intervector) pacing delays by identifying the conduction delay that corresponds to the particular pair of vectors to be used for pacing. In circumstances where more than one interelectrode conduction delay might be found to generally "correspond" to a given vector pair, the device can be programmed to select one of the applicable interelectrode conduction delays for use in setting the pacing delay for that vector pair (such as by choosing the shortest of the interelectrode delays that applies), or based on resulting hemodynamics. As already noted, any pacing delays found to exceed 80 ms are rejected. This value, also, can be programmable and adjustable by the clinician. Note also that, if the device is equipped to exploit various pacing vector permutations, the pacing delay value determined between a given pair of vectors can be used as the pacing delay between any vector permutation having that pair of vectors as one of its components.

Procedure (2) is generally similar to procedure (1) but the pacing delay is set based on interelectrode conduction delays obtained during single-site RV pacing, rather than single-site LV pacing. Also, with procedure (2), the pacing delay can be set equal to the corresponding conduction delay or, depending upon device programming, to a value less than conduction delay by, e.g., using a suitable scaling factor (such as a value programmed in the range of 5%-95%.) The scaling factor used for conduction delays obtained from single-site RV pacing can differ from that of single-site LV pacing. Again, otherwise routine experimentation can be employed in advance to determine a preferred or optimal value for the scaling factor, which is then programmed into the device for use with the patient, subject to clinician review.

Procedure (3) is generally similar to procedure (2) but the pacing delay is set within a range of ±X % around the corresponding interelectrode conduction delay or within a range of ±X where X represents a time value rather than a percentage value. A suitable time value for X is 10 ms. As with the aforementioned scaling factors, otherwise routine experimentation can be employed to determine a preferred or optimal value for X, which is then programmed into the device for use with the patient, subject to clinician review.

Procedure (4) is also generally similar to procedure (1) but the pacing delay is set based on interelectrode conduction delays obtained during sinus rhythm, rather than during LV pacing. Also, with procedure (4), the pacing delay can be set equal to the corresponding conduction delay or, depending upon device programming, to a value less than conduction delay by, e.g., using a suitable scaling factor (such as a value programmed again in the range of 5%-95%.) The scaling factor used for conduction delays obtained during sinus rhythm can differ from that of single-site LV pacing or single-site RV pacing. Again, otherwise routine experimentation can be employed to determine a preferred or optimal value for the scaling factor, which is then programmed into the device for use with the patient, subject to clinician review.

Procedure (5) is generally similar to procedure (4) but the pacing delay is set within a range of ±Y % around the corresponding interelectrode conduction delay or within a range of ±Y where Y represents a time value rather than a percentage value. As with the aforementioned scaling factors, otherwise routine experimentation can be employed in advance to determine a preferred or optimal value for Y, which is then programmed into the device for use with the patient, subject to clinician review. Note that the value for Y can be the same as that of X (discussed above) or it might be different, depending upon device programming or other factors.

Note that, if several different procedures are used by the device to determine a given pacing delay for a particular pair of vectors, the various individual delay values obtained for that particular pair of vectors using the different procedures can be combined, in at least some cases, to yield a single delay value for use with that particular pair of vectors. Note also that 80 ms is just one exemplary maximum value, which is particularly appropriate for LV pre-excitation. In other cases, such as with RV pre-excitation, a different maximum value might be preferred, such as 50 ms.

At step 203, the device, having determined a set of pacing delays that should be effective, now identifies and rejects any of specific pacing delays that trigger adverse cardiac effects, such as delays that trigger arrhythmias or delays that cause irregular activation in the RV or LV. Techniques for detecting adverse cardiac effects will be described below with reference to FIG. 4.

At step 204, the device, having determined suitable pacing delays, now selects an optimal electrode combination or vectors permutations that provides the highest or best pacing efficacy during MSLV pacing, such the vector permutation that provides the best hemodynamic response. Techniques for identifying optimal electrode combination or vectors permutations based on pacing efficacy will be described below with reference to FIG. 5.

In an alternative implementation, rather than determining the pacing delays first and then identifying the optimal pacing vectors, the device performs these steps together. This will be described with reference to FIG. 6.

At step 206, the device then delivers MSLV pacing while employing the MSLV interelectrode pacing delays determined at step 202 and while using the optimal combination/permutation of electrodes/vectors selected at step 204. As already explained, this pacing may be coordinated with RV pacing to provide CRT. The MSLV interelectrode pacing delays are typically employed in addition to any AV/PV or VV pacing delays used by the device during CRT.

Figure 4:
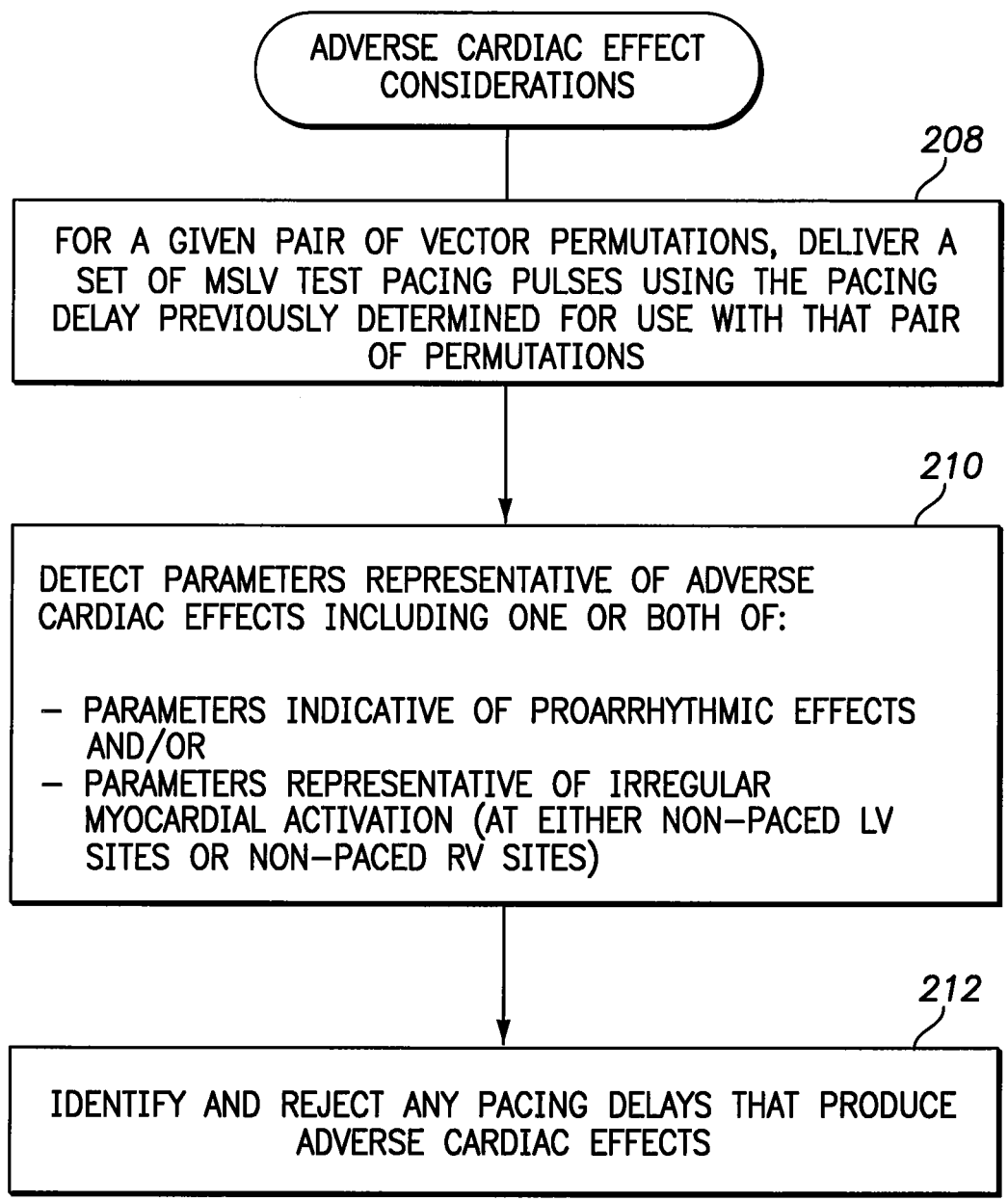
FIG. 4 particularly illustrates techniques for assessing adverse cardiac effects that may be exploited by the implementation of FIG. 3.

Turning now to FIG. 4, an exemplary technique for use at step 204 of FIG. 3 will be described for identifying and rejecting any pacing delays that produce adverse cardiac effects. At step 208, for a given pair of pacing vector permutations, the device delivers a set of MSLV test pacing pulses using the pacing delay previously determined for use with that pair of permutations (i.e. the pacing delay determined at step 202 of FIG. 3.) At step 210, the device detects parameters representative of possible adverse cardiac effects including one or both of:
  parameters indicative of proarrhythmic effects, and/or
  parameters representative of irregular myocardial activation (at either non-paced LV sites or non-paced RV sites).

Thus, for example, the device can track parameters such as atrial and ventricular rates, various cardiac event intervals and/or cardiac waveform morphology to detect possible arrhythmias. Otherwise routine arrhythmia detection techniques can be used, which are well known in the art. For the purposes of detecting irregular myocardial activation, the device can examine various parameters derived from IEGM channels to detect possible irregularities in myocardial activation (i.e. depolarization) such as by detecting the onset of premature ventricular contractions (PVCs) or the like or by detecting parameters representative of the fractionation of the IEGM. Otherwise routine techniques can be used for detecting irregular myocardial activation, which are also well known in the art.

At step 212, the device then identifies and rejects any pacing delays that produce adverse cardiac effects. For example, if an arrhythmia is detected during the delivery of the test pacing pulses using a given pacing delay, then that delay is deemed to be proarrhythmic and is rejected. In some examples, the test might be repeated to make sure the arrhythmia is indeed due to the pacing delay and not some other coincidental factor. Likewise, if irregular myocardial activation is detected during the delivery of the test pacing pulses using a given pacing delay, then that delay is deemed to have caused the irregular activation and is rejected. The test can be repeated to make sure the irregular activation is indeed due to the pacing delay and not some other coincidental factor.

FIG. 5 illustrates an exemplary technique for use at step 204 of FIG. 3 for selecting a preferred or optimal electrode combination or vector permutation that provides the highest pacing efficacy during MSLV pacing. At step 214, the device delivers a set of MSLV test pacing pulses using selected permutations of LV pacing vectors chosen, for example, from: LV tip-RV coil; LV ring1-RV coil; LV ring2-RV COIL; LV ring3-RV coil; LV tip-LV ring1; LV tip-LV ring3; LV ring1-LV ring3; LV ring2-LV ring1; LV ring2-LV ring3; and LV ring3-LV ring1. This is the same quadra-pole list of vectors provided above and is merely exemplary. The particular set of permutations to be used can be preprogrammed into the device subject to clinician review. For each selected permutation, the device delivers some predetermined number of test pacing pulses (likewise a programmable number) sufficient to allow cardiac pacing efficacy to be assessed. The test pacing pulses are preferably delivered using the optimal MSLV interelectrode pacing delays previously determined at step 202 of FIG. 3 (excluding any delays found to produce adverse cardiac effects as determined at step 203 of FIG. 3.)

At step 216, the device detects parameters representative of possible pacing efficacy for each permutation including one or more of:
  quickest activation time to non-paced sites in the LV or RV
  shortest QRS duration (at nonpaced sites in the LV or RV)
  least degree of LV or RV IEGM fractionation
  best hemodynamic response (as detected by the implanted device or by an external device)

The activation time delay represents the time from delivery of V-pulses to a resulting depolarization and can be measured at any nonpaced site in the LV or RV. The vector permutation that yields the quickest activation times is preferred. In some examples, only RV activation times might be assessed. In other examples, only LV activation times might be assessed. QRS duration represents the "width" or time duration of a paced QRS detected at a location other than the pacing site. LV or RV QRS duration (or both) can be tracked. The vector permutation that yields the shortest QRS durations is preferred. Insofar as fractionation is concerned, LV and/or RV IEGM signals (sensed at various sites) can be examined to assess a degree of fractionation of the cardiac signal. The degree of fractionation relates to the degree of continuity of the paced QRS (or an evoked response) and may be quantified by template matching, feature characterization, or frequency information such as fast Fourier transform (FFT) spectra, all of which are well known in the art. See, for example, U.S. Pat. No. 7,440,804 to Min, et al. Fractionation can also be assessed based on cardiogenic impedance signals. See, for example, U.S. Patent Application 2008/0262361 of Gutfinger et al. When used in conjunction with an external monitor, any of these parameters might instead be detected by the external monitor and then transmitted to the implanted device for processing therein (and/or the parameters could be transferred to an external programmer for use therein in controlling the optimization procedure.)

Additionally, depending upon the capabilities of the device, some measure of hemodynamic response can be assessed by the device itself, such as cardiac output, stroke volume, left atrial pressure or some suitable measure of cardiogenic impedance. See, for example, U.S. Pat. No. 7,139,609 to Min, et al. In some examples, an external monitor is used to assess hemodynamic response and the parameters representative of that response are transmitted to the implanted device for processing therein (and/or the parameters could be transferred to an external programmer for use therein in controlling the optimization procedure.)

At step 218, the device then identifies and selects any permutations of pacing vectors that yield the greatest pacing efficacy. If several different parameters representative of pacing efficacy are measured by the device, these parameters can be combined so as to produce a single "metric" value for assessing the overall degree of pacing efficacy of the pacing vector permutations.

Figure 6:
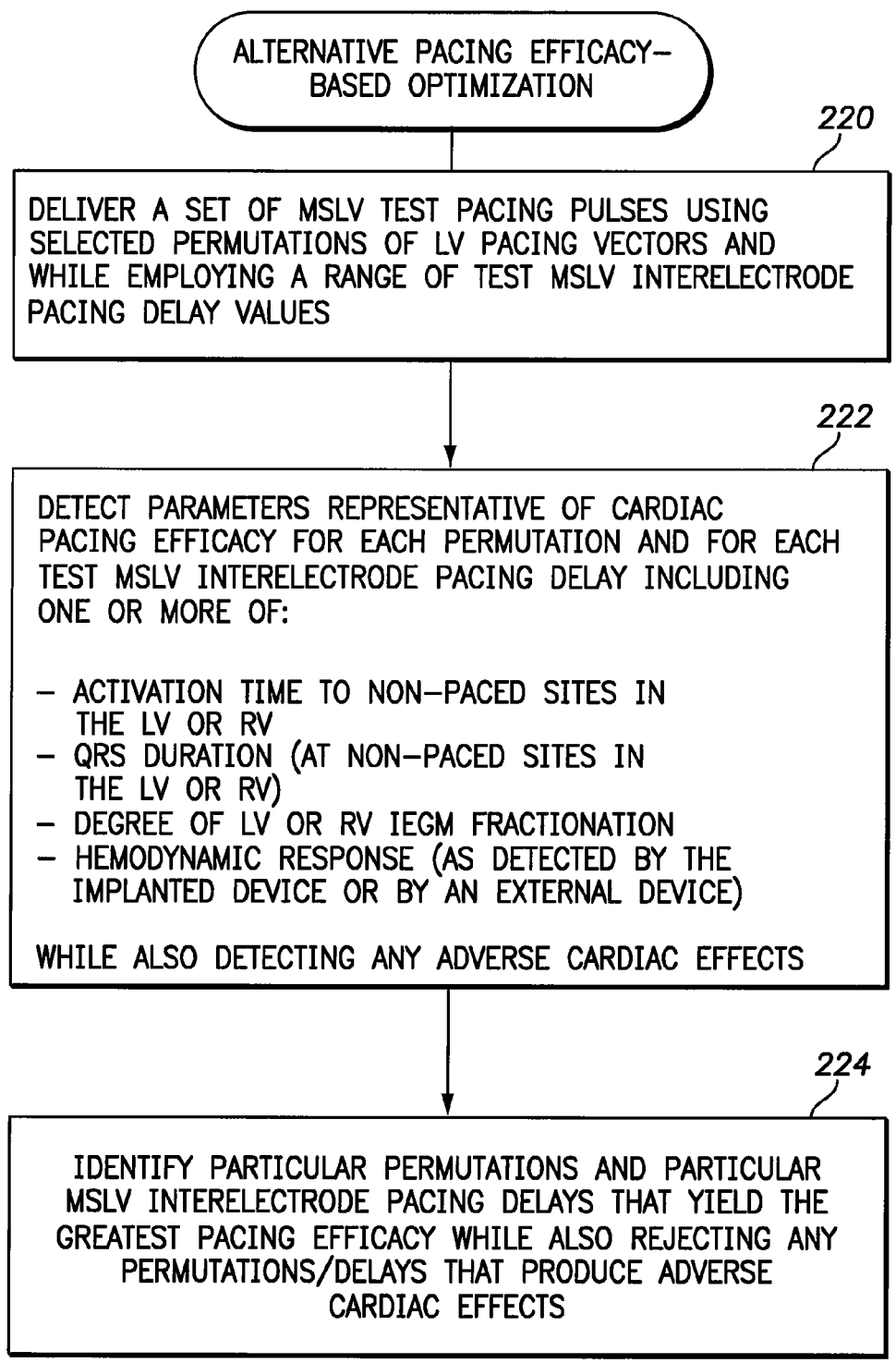
FIG. 6 illustrates an alternative technique for assessing pacing efficacy that may be exploited by the implementation of FIG. 3, wherein test pacing pulses are delivered throughout a range of different MSLV interelectrode pacing delays while using various different pacing vector permutations in order to identify an optimal combination of MSLV pacing delay and pacing vector permutation.

FIG. 6 illustrates an alternative technique for use at steps 202 and 204 of FIG. 3 for selecting preferred or optimal vector permutations and interelectrode pacing delays that provide the highest pacing efficacy during MSLV pacing (while also avoiding adverse cardiac effects.) Some of the steps of FIG. 6 are similar to those of FIGS. 4 and 5 and will not be described again in detail. At step 220, the device delivers a set of MSLV test pacing pulses using selected permutations of LV pacing vectors and while employing a range of test pacing delay values. That is, for each pair of pacing vector permutations, the device sequential delivers a set of test pacing pulses over a range of pacing delays, such as from 0 ms to 80 ms. For each selected pair of permutations and for each pacing delay value within the range, the device delivers a sufficient number of test pacing pulses to allow pacing efficacy to be detected or otherwise assessed by the implanted device (or by an external system) and to allow any adverse cardiac effects to be detected.

At step 222, the device detects parameters representative of cardiac pacing efficacy for each permutation and for each test pacing delay value, including one or more of:
  activation time to non-paced sites in the LV or RV
  QRS duration (at nonpaced sites in the LV or RV)
  degree of LV or RV IEGM fractionation
  hemodynamic response (as detected by the implanted device or by an external device.)
while also detecting any adverse cardiac effects, such as arrhythmias or irregular cardiac activation. The evaluation of pacing efficacy parameters is discussed above with reference to FIG. 5. The detection of adverse cardiac effects is discussed above with reference to FIG. 4.

At step 224, the device then identifies and selects particular permutations of pacing vectors and a particular MSLV interelectrode pacing delay values that yield the greatest pacing efficacy (while also rejecting any permutations/delays that produce adverse cardiac effects.) If several different parameters representative of pacing efficacy are measured, these parameters can be combined so as to produce a single "metric" value for assessing the overall degree of pacing efficacy. Likewise, if several different parameters representative of adverse cardiac effects are measured, these parameters can be combined so as to produce a single "metric" value for assessing the overall adverse cardiac effect. Thereafter, step 206 of FIG. 3 is performed where MSLV pacing (such as MSLV CRT) is delivered using optimal combinations of interelectrode pacing delay and pacing vector permutations.

Hence, FIGS. 2-6 illustrate various techniques for optimizing MSLV pacing for use when interelectrode pacing delays are to be employed (i.e. when multisite LV pacing is employed with adjustable interelectrode and/or intervector pacing delays.) Additionally or alternatively, various techniques can be employed for use in optimizing MSLV pacing when interelectrode pacing delays are not used or when single-site pacing is employed in the LV. For the sake of completeness, these techniques will now be summarized with reference to FIGS. 7 and 8.

Single-Site Pacing in the LV

As shown in by step 250 of FIG. 7, when single-site LV pacing is implemented in a device that supports multi-polar LV pacing, the following criteria for selecting the optimal single site can be used:
  1) Pacing site and pacing vector that yields no significant phrenic nerve stimulation 2) Pacing site and pacing vector that yields the lowest pacing capture threshold
3) Pacing site that yields the largest amplitude of sensed electrogram
4) Pacing site that yields the shortest activation to the RV sensed channel after testing all pacing vectors at each LV site
5) Pacing site that yields the shortest activation to the rest of LV sensed channels after testing all pacing vectors at each LV site
6) Pacing site that yields minimum variability in interelectrode timing delays between LV electrodes when paced at each LV site
   Ex., when distal tip is being paced DT1=tip–R1, DT2=R1–R2; DT3=R2–R3, calculate standard deviation (SD1) of DT1:DT3. When R1 is being paced, DT1=R1–tip, DT2=R1–R2, DT3=R2–R3–SD2=DT1:DT3. When R2 is being paced, DT1=R2–R1, DT2=R1–tip, DT3=R2–R3–SD3=DT1:DT3. When R3 is being paced, DT1=R3–R2, DT2=R2–R1, DT3=R1–tip–SD4=DT1:DT3.
7) Pacing site that yields no fractionation (or less fractionated) electrograms detected on the rest of LV sensed channels
   a. This can be assessed by measuring the duration of the electrograms or morphology-based analysis of the electrograms
8) Pacing site that yields sequential activation, no multidirectional activation detected on the rest of LV sensed channels
   Ex., when distal electrode is paced, the direction of activation should be distal to proximal based on the activation time picked at each electrode or the morphology of the electrograms detected at each site. Morphological determination can be achieved by assessing the "positiveness" and "negativeness" of unipolar electrograms detected at each site.
9) Pacing site that yields optimal hemodynamic response (e.g., cardiogenic impedance, left atrial pressure) as measured by the device or an external system
10) Pacing site that yields no proarrhythmic events Item number 1) addresses phrenic nerve stimulation avoidance; numbers 2-3) address long-term pacing management; number 4) addresses interventricular timing optimization; numbers 5-8) address intraventricular timing optimization; and number 9) address hemodynamic optimization. The clinician may select the particular criteria to be implemented/considered while programming the device for each device recipient. In some implementations, the optimization can be done automatically by pressing just one button on the programmer screen.

Multi-Site Pacing in the LV (without MSLV Interelectrode Pacing Delays)

As shown in by step 252 of FIG. 8, when multisite pacing is to be delivered substantially simultaneously in the LV (i.e., at some minimum interelectrode pacing delay, such as 4 ms) in a device that supports the multipolar LV pacing, the following criteria for selecting the optimal permutation can be used:

1) The permutation that yields no significant phrenic nerve stimulation
2) The permutation that yields lowest combined pacing capture threshold
3) The permutation that has highest combined sensed electrogram amplitude
4) The permutation that yields the shortest activation to the RV sensed channel
5) The permutation that yields optimal hemodynamic response (e.g., cardiogenic impedance, left atrial pressure) as measured by the device or an external system
6) The permutation that yields no fractionation (or less fractionation) of electrogram at non-paced sites
7) The permutation that yields the quickest activation to non-paced sites
8) The permutation that produces no proarrhythmic events Again, the clinician may select the particular criteria to be implemented/considered while programming the device for each device recipient. In some implementations, the optimization can be done automatically by pressing just one button on the programmer screen.

Thus, various techniques have been described for optimizing pacing for use with a multiple LV lead. Although primarily described with respect to examples having a pacer/ICD, other implantable medical devices may be equipped to exploit the techniques described herein such as CRT devices and CRT-D devices (i.e. a CRT device also equipped to deliver defibrillation shocks.) For the sake of completeness, an exemplary pacer/ICD will now be described, which includes components for performing the functions and steps already described.

Exemplary Pacer/ICD

Figure 9:
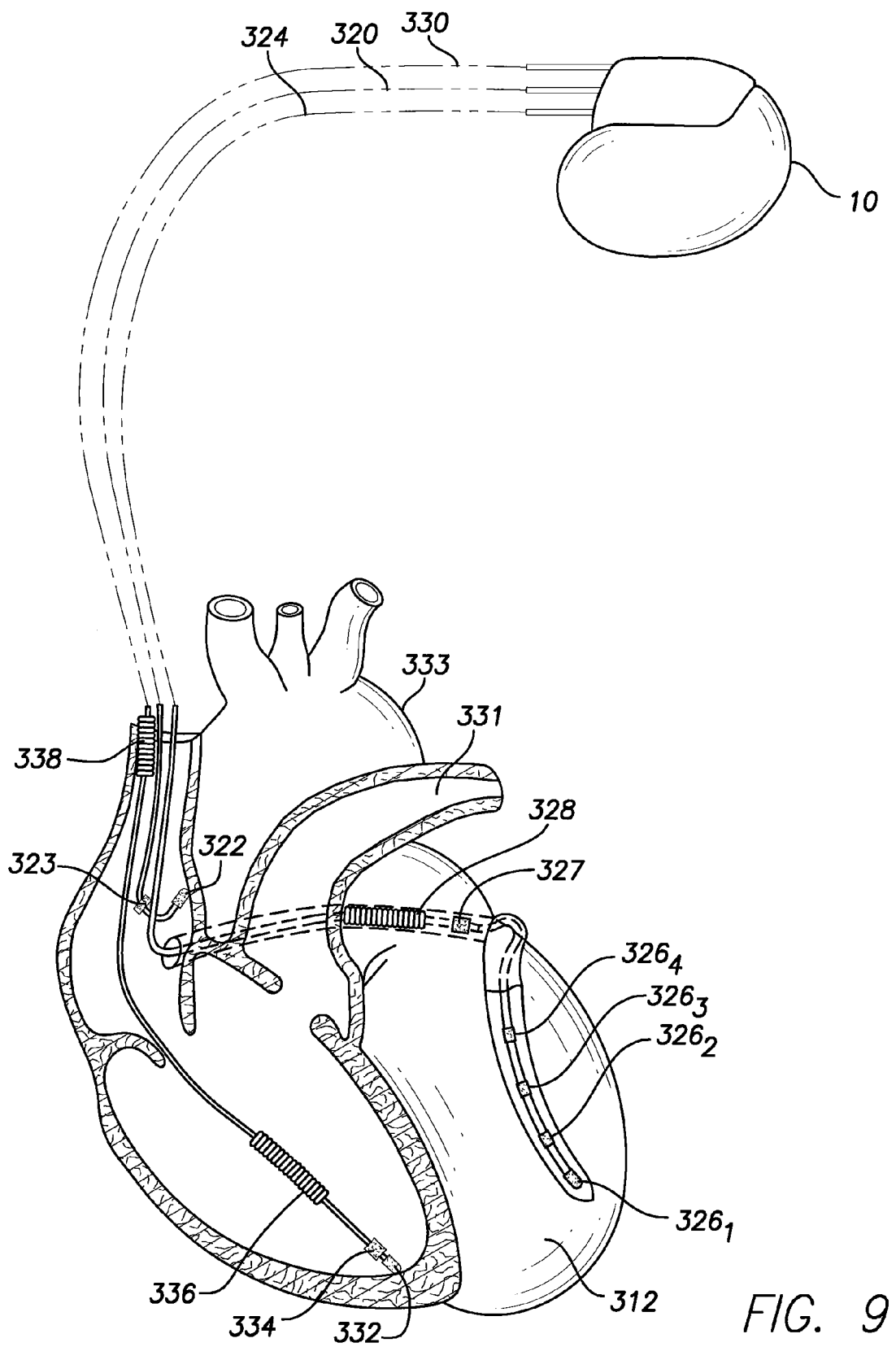
FIG. 9 is a simplified, partly cutaway view, illustrating the device of FIG. 1 along with at set of leads implanted into the heart of the patient.
Figure 10:
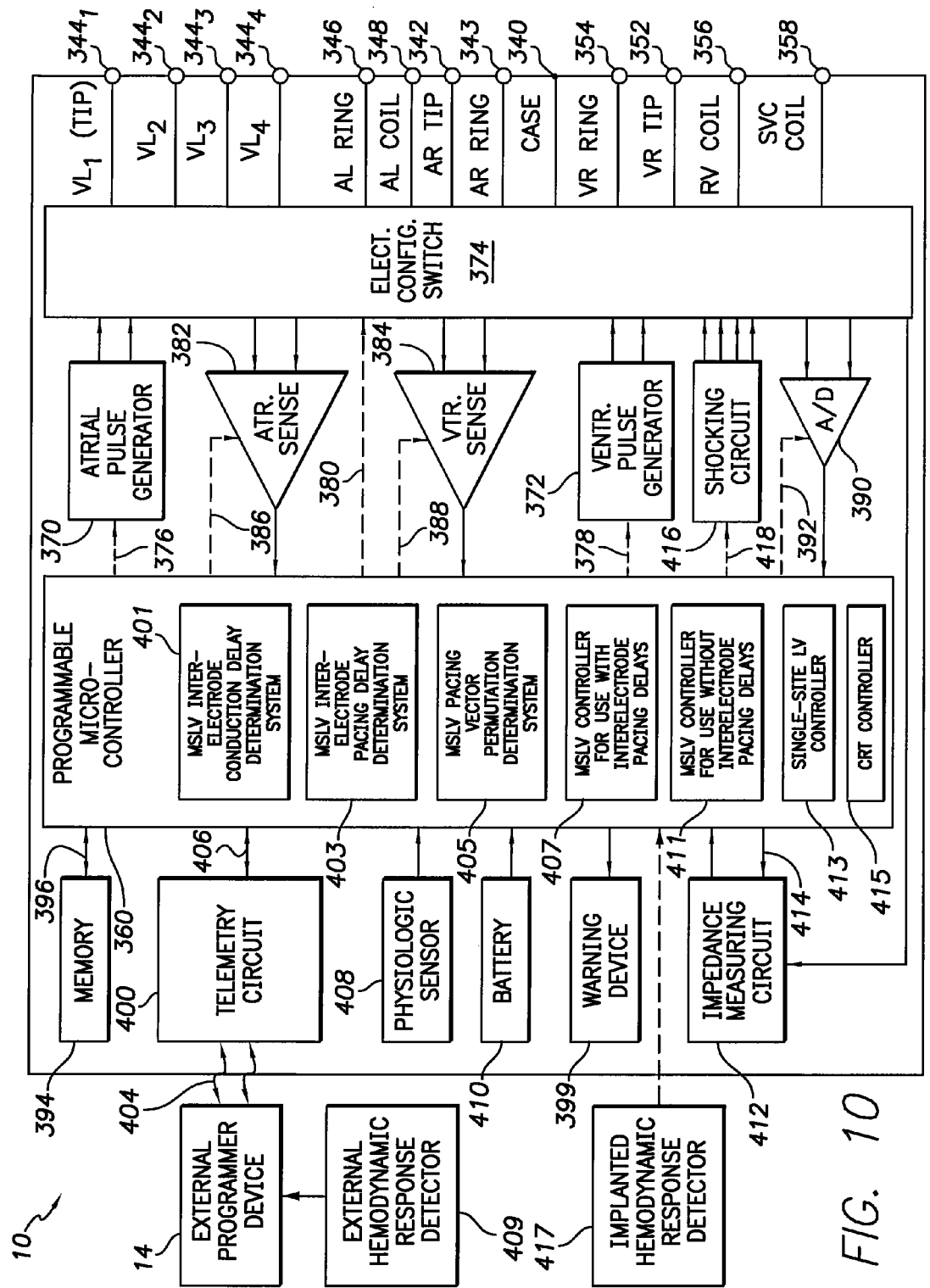
FIG. 10 is a functional block diagram of the pacer/ICD of FIG. 9, illustrating basic circuit elements that provide cardioversion, defibrillation and/or pacing stimulation in the heart an particularly illustrating on-board optimization components for controlling the techniques of FIGS. 2-8.

With reference to FIGS. 9 and 10, a description of an exemplary pacer/ICD will now be provided. FIG. 9 provides a simplified block diagram of the pacer/ICD, which is a dual-chamber stimulation device capable of treating both fast and slow arrhythmias with stimulation therapy, including cardioversion, defibrillation, and pacing stimulation, and also capable of setting and using VV pacing delays, as discussed above. To provide other atrial chamber pacing stimulation and sensing, pacer/ICD 10 is shown in electrical communication with a heart 312 by way of a left atrial lead 320 having an atrial tip electrode 322 and an atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a multi-pole LV lead 324 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 324 is designed to receive atrial and ventricular cardiac signals and to deliver left ventricular pacing therapy using a set of four left ventricular electrodes $326_1$, $326_2$, $326_3$, and $326_4$ (thereby providing a Quadra-pole lead), left atrial pacing therapy using at least a left atrial ring electrode 327, and shocking therapy using at least a left atrial coil electrode 328. The $326_1$ LV electrode may also be referred to as a "tip" or "distal" LV electrode. The $326_4$ LV electrode may also be referred to as a "proximal" LV electrode. In other examples, more or fewer LV electrodes are provided. Although only three leads are shown in FIG. 9, it should also be understood that additional leads (with one or more pacing, sensing and/or shocking electrodes) might be used and/or additional electrodes might be provided on the leads already shown, such as additional electrodes on the RV lead.

A simplified block diagram of internal components of pacer/ICD 10 is shown in FIG. 10. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 340 for pacer/ICD 10, shown schematically in FIG. 10, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, $344_1$-$344_4$, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 323. To achieve left chamber sensing, pacing and shocking, the connector includes a left ventricular tip terminal ($VL_1$ TIP) $344_1$ and additional LV electrode terminals $344_2$-$344_4$ for the other LV electrodes of the Quadra-pole LV lead.

The connector also includes a left atrial ring terminal ($A_L$ RING) 346 and a left atrial shocking terminal ($A_L$ COIL) 348, which are adapted for connection to the left atrial ring electrode 327 and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($V_R$ COIL) 356, and an SVC shocking terminal (SVC COIL) 358, which are adapted for connection to the right ventricular tip electrode 332, right ventricular ring electrode 334, the $V_R$ coil electrode 336, and the SVC coil electrode 338, respectively. Although not shown in the figure, additional terminals can be provided to accommodate any sub-Q electrodes that might be provided as part of the implantable system.

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 10, an atrial pulse generator 370 and a ventricular pulse generator 372 generate pacing stimulation pulses for delivery by the right atrial lead 320, the right ventricular lead 330, and/or the LV lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 382 and ventricular sensing circuits 384 may also be selectively coupled to the right atrial lead 320, LV lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, pacer/ICD 10 utilizes the atrial and ventricular sensing circuits, 382 and 384, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the right atrial lead 320, the LV lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 394 through a telemetry circuit 400 in telemetric communication with the external device 402, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 10 (as contained in the microcontroller 360 or memory 394) to be sent to the external device 402 through an established communication link 404. Pacer/ICD 10 further includes an accelerometer or other physiologic sensor 408, commonly referred to as a "rate-responsive" sensor because it is typically used to adjust pacing stimulation rate according to the exercise state of the patient. However, the physiological sensor 408 may further be used to detect changes in cardiac output, changes in the physiological condition of the heart, or diurnal changes in activity (e.g., detecting sleep and wake states) and to detect arousal from sleep. Accordingly, the microcontroller 360 responds by adjusting the various pacing parameters (such as rate, AV delay, VV delay, etc.) at which the atrial and ventricular pulse generators, 370 and 372, generate stimulation pulses. While shown as being included within pacer/ICD 10, it is to be understood that the physiologic sensor 408 may also be external to pacer/ICD 10, yet still be implanted within or carried by the patient. A common type of rate responsive sensor is an activity sensor incorporating an accelerometer or a piezoelectric crystal, which is mounted within the housing 340 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 410, which provides operating power to all of the circuits shown in FIG. 10. The battery 410 may vary depending on the capabilities of pacer/ICD 10. If the system only provides low voltage therapy, a lithium iodine or lithium copper fluoride cell typically may be utilized. For pacer/ICD 10, which employs shocking therapy, the battery 410 should be capable of operating at low current drains for long periods, and then be capable of providing high-current pulses (for capacitor charging) when the patient requires a shock pulse. The battery 410 should also have a predictable discharge characteristic so that elective replacement time can be detected. Accordingly, appropriate batteries are employed.

As further shown in FIG. 10, pacer/ICD 10 is shown as having an impedance measuring circuit 412, which is enabled by the microcontroller 360 via a control signal 414. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 412 is advantageously coupled to the switch 474 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

An internal warning device 399 may be provided for generating perceptible warning signals to the patient via vibration, voltage or other methods.

Insofar as MSLV pacing is concerned, the microcontroller includes an MSLV interelectrode conduction delay determination system 401 operative to determine MSLV interelectrode conduction delays among the electrodes of the multi-pole LV lead of FIG. 9. An MSLV interelectrode pacing delay determination system 403 is operative to set MSLV interelectrode (i.e. intervector) pacing delays based on the MSLV interelectrode conduction delays for use in delivering MSLV pacing using the multi-pole LV lead, such as by using the pacing delay optimization techniques described above. An MSLV pacing vector permutation determination system 405 is operative to select MSLV pacing vector permutations using the permutation selection techniques described above. An MSLV controller 407 is operative to control MSLV pacing when using the MSLV interelectrode pacing delays determined by system 403.

Additionally, the microcontroller can include an MSLV controller for use without interelectrode pacing delays, which is operative to select pacing vector permutations in accordance with the techniques of FIG. 8, discussed above. The microcontroller can also include a single-site LV controller, which is operative to select pacing sites in accordance with the techniques of FIG. 7, discussed above. A CRT controller 415 is operative to control delivery of CRT (in conjunction with the various MSLV/single-site controllers.) Diagnostic information pertinent to the various optimization procedures may be stored in memory 394.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

In some examples, the device uses hemodynamic response data received from an external hemodynamic response monitor 409 or from an implanted hemodynamic response monitor 417. Other external monitors can additionally or alternatively be used.

As noted, at least some of the techniques described herein can be performed by (or under the control of) an external device. For the sake of completeness, a detailed description of an exemplary device programmer will now be provided.

Exemplary External Programmer

Figure 11:
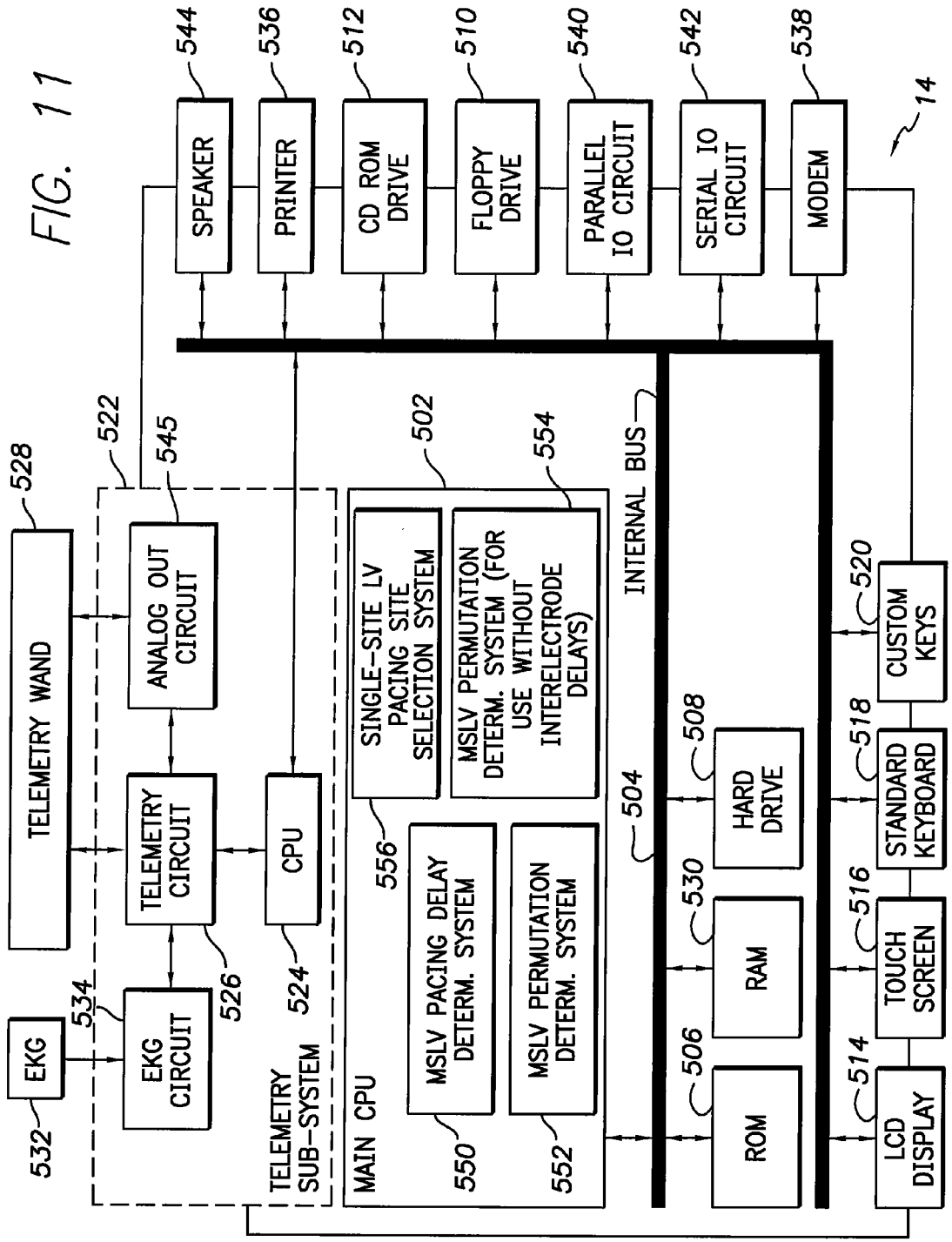
FIG. 11 is a functional block diagram illustrating components of the external device programmer of FIG. 1 and particularly illustrating programmer-based systems for controlling the techniques of FIGS. 2-9.

FIG. 11 illustrates pertinent components of an external programmer 14 for use in programming the pacer/ICD of FIGS. 9 and 10 and for performing the above-described optimization techniques. For the sake of completeness, other device programming functions are also described herein. Generally, the programmer permits a physician, clinician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 14 may also be capable of processing and analyzing data received from the implanted device and from the EKG leads to, for example, render preliminary diagnosis as to medical conditions of the patient or to the operations of the implanted device.

Now, considering the components of programmer 14, operations of the programmer are controlled by a CPU 502, which may be a generally programmable microprocessor or microcontroller or may be a dedicated processing device such as an application specific integrated circuit (ASIC) or the like. Software instructions to be performed by the CPU are accessed via an internal bus 504 from a read only memory (ROM) 506 and random access memory 530. Additional software may be accessed from a hard drive 508, floppy drive 510, and CD ROM drive 512, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 514 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 516 overlaid on the LCD display or through a standard keyboard 518 supplemented by additional custom keys 520, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 14 to retrieve data stored within any implanted devices and to also retrieve EKG data from EKG leads, if any, coupled to the patient. To this end, CPU 502 transmits appropriate signals to a telemetry subsystem 522, which provides components for directly interfacing with the implanted devices, and the EKG leads. Telemetry subsystem 522 includes its own separate CPU 524 for coordinating the operations of the telemetry subsystem. Main CPU 502 of programmer communicates with telemetry subsystem CPU 524 via internal bus 504. Telemetry subsystem additionally includes a telemetry circuit 526 connected to telemetry wand 528, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an EKG circuit 534 for receiving surface EKG signals from a surface EKG system 532. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the pacer/ICD also includes the data stored within the recalibration database of the pacer/ICD (assuming the pacer/ICD is equipped to store that data.) Data retrieved from the implanted devices is stored by external programmer 14 either within a random access memory (RAM) 530, hard drive 508 or within a floppy diskette placed within floppy drive 510. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 14, the implanted devices may be further controlled to transmit additional data in real time as it is detected by the implanted devices, such as additional IEGM data, lead impedance data, and the like. Additionally, or in the alternative, telemetry subsystem 522 receives EKG signals from EKG leads 532 via an EKG processing circuit 534. As with data retrieved from the implanted device itself, signals received from the EKG leads are stored within one or more of the storage devices of the external programmer. Typically, EKG leads output analog electrical signals representative of the EKG. Accordingly, EKG circuit 534 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 502, the programming commands are converted to specific programmable parameters for transmission to the implanted devices via telemetry wand 528 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 536.

Programmer/monitor 14 also includes a modem 538 to permit direct transmission of data to other programmers via the public switched telephone network (PSTN) or other interconnection line, such as a T1 line or fiber optic cable. Depending upon the implementation, the modem may be connected directly to internal bus 504 may be connected to the internal bus via either a parallel port 540 or a serial port 542. Other peripheral devices may be connected to the external programmer via parallel port 540 or a serial port 542 as well. Although one of each is shown, a plurality of input output (IO) ports might be provided. A speaker 544 is included for providing audible tones to the user, such as a warning beep in the event improper input is provided by the physician. Telemetry subsystem 522 additionally includes an analog output circuit 545 for controlling the transmission of analog output signals, such as IEGM signals output to an EKG machine or chart recorder.

Insofar as MSLV pacing is concerned, main CPU 502 includes an MSLV pacing delay determination system 550 operative to set MSLV interelectrode pacing delays based on MSLV interelectrode conduction delays for use in programming the implanted device to delivery MSLV pacing using the multi-pole LV lead, such as by using the pacing delay optimization techniques described above. The MSLV interelectrode conduction delays can be determined, for example, by the external programmer by examining IEGM signals received from the pacer/ICD. Alternatively, the interelectrode conduction delays can be determined by the implanted device, then transmitted to the external programmer. In any case, the MSLV interelectrode pacing delays are then programmed into the implanted device for use therein. An MSLV pacing vector permutation determination system 552 is operative to select MSLV pacing vector permutations using the permutation selection techniques described above. The selected permutations are then programmed into the implanted device for use therein.

Additionally, the CPU can include an MSLV controller 554 for use without interelectrode pacing delays, which is operative to select pacing vector permutations in accordance with the techniques of FIG. 8, discussed above, for programming into the implanted device. The CPU can also include a single-site LV controller 556, which is operative to select pacing sites in accordance with the techniques of FIG. 7, discussed above, for programming the implanted device.

Depending upon the implementation, the various components of the CPU may be implemented as separate software modules or the modules may be combined to permit a single module to perform multiple functions. In addition, although shown as being components of the CPU, some or all of these components may be implemented separately, using ASICs or the like.

Note that, in at least some examples, the MSLV optimization components employ information received by the external programmer from external monitoring devices, such as external hemodynamic monitors. Such information can be input via the various input systems already noted, such as the parallel or serial IO circuits.

With the programmer configured as shown, a clinician or other user operating the external programmer is capable of retrieving, processing and displaying a wide range of information received from the implanted device and to reprogram the implanted device if needed. In many implementations, the clinician may be able to optimize MSLV pacing merely by pushing one button on the external programmer input screen, which activates a pre-programmed optimization procedure that exploits the techniques described above. As such, MSLV optimization becomes a relatively simple matter for the clinician.

The descriptions provided herein with respect to FIG. 10 are intended merely to provide an overview of the operation of programmer and are not intended to describe in detail every feature of the hardware and software of the programmer and is not intended to provide an exhaustive list of the functions performed by the programmer.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable cardiac stimulation device equipped for multi-site left ventricular (MSLV) pacing using a multi-pole LV lead, the method comprising:
    determining MSLV interelectrode conduction delays between detection of events at different LV electrodes from a plurality of LV electrodes of the multi-pole LV lead;
    setting MSLV interelectrode pacing delays based on the MSLV interelectrode conduction delays for use in delivering MSLV pacing along corresponding pacing vectors using the multi-pole LV lead; and
    controlling MSLV pacing for the corresponding pacing vectors using the MSLV interelectrode pacing delays.

2. The method of claim 1 wherein the steps are performed by the implantable cardiac stimulation device.

3. The method of claim 1, for use with an implantable device also equipped with a right ventricular (RV) lead, wherein MSLV pacing is delivered in conjunction with RV pacing.

4. The method of claim 1 including rejecting any MSLV interelectrode pacing delays for use in MSLV pacing that produce adverse cardiac pacing effects.

5. The method of claim 4 wherein the adverse cardiac pacing effects include one or more of proarrhythmic effects, irregular activation effects at non-paced sites in the LV, and irregular activation effects at non-paced sites in the right ventricle (RV).

6. The method of claim 1 wherein the MSLV interelectrode conduction delays are determined during single-site LV pacing.

7. The method of claim 1 wherein the MSLV interelectrode conduction delays are determined during single-site RV pacing.

8. The method of claim 1 wherein the MSLV interelectrode conduction delays are determined during sinus rhythm.

9. The method of claim 8 wherein the MSLV interelectrode pacing delays are set to values no greater than corresponding MSLV interelectrode conduction delays determined during sinus rhythm.

10. The method of claim 1 further including determining a combination of pacing vectors for use in delivering MSLV pacing using the multi-pole LV lead.

11. The method of claim 1 further including:
delivering MSLV test pacing pulses over a range of MSLV interelectrode pacing delay values;
detecting one or more parameters representative of MSLV pacing efficacy for each MSLV interelectrode pacing delay value; and
identifying a particular MSLV interelectrode pacing delay value that yields the greatest pacing efficacy for use in delivering further MSLV pacing.

12. The method of claim 11 further including:
delivering MSLV test pacing pulses using a plurality of different pacing vector permutations;
detecting one or more parameters representative of MSLV pacing efficacy for each combination of MSLV interelectrode pacing delay value and pacing vector permutation; and
identifying a particular combination of MSLV interelectrode pacing delay value and vector permutation that yields the greatest pacing efficacy for use in delivering further MSLV pacing.

13. The method of claim 1, wherein the determining operation determines the MSLV interelectrode conduction delays between pairs of the LV electrodes from the plurality of electrodes of the multi-pole LV lead.

14. The method of claim 1, wherein the MSLV interelectrode conduction delays represent time delays between detection of electrocardiac events at different ones of the plurality of LV electrodes.

15. The method of claim 1, wherein at least one of the pacing vectors is between a pair of LV electrodes from the plurality of electrodes.

16. The method of claim 1, wherein the MSLV interelectrode pacing delays represent time delays to be employed during MSLV pacing between pulses delivered along the pacing vectors.

17. A system for use with an implantable cardiac stimulation device equipped for multi-site left ventricular (MSLV) pacing using a multi-pole LV lead, the system comprising:
an MSLV interelectrode conduction delay determination system operative to determine MSLV interelectrode conduction delays between detection of events at different LV electrodes from a plurality of LV electrodes of the multi-pole LV lead;
an MSLV interelectrode pacing delay determination system operative to set MSLV interelectrode pacing delays based on the MSLV interelectrode conduction delays for use in delivering MSLV pacing along corresponding pacing vectors using the multi-pole LV lead; and
an MSLV pacing controller operative to control MSLV pacing for the corresponding pacing vectors using the MSLV interelectrode pacing delays.

18. The system of claim 17 wherein the claimed components are components of the implantable cardiac stimulation device.

19. The system of claim 17, wherein the MSLV interelectrode conduction delay determination system is operative to determine the MSLV interelectrode conduction delays between pairs of the LV electrodes from the plurality of electrodes of the multi-pole LV lead.

20. The system of claim 17, wherein the MSLV interelectrode conduction delays represent time delays between detection of electrocardiac events at different ones of the plurality of LV electrodes.

21. The system of claim 17, wherein at least one of the pacing vectors is between a pair of LV electrodes from the plurality of electrodes.

22. The system of claim 17, wherein the MSLV interelectrode pacing delays represent time delays to be employed during MSLV pacing between pulses delivered along the pacing vectors.

23. A system for use with an implantable cardiac stimulation device equipped for multi-site left ventricular (MSLV) pacing using a multi-pole LV lead, the system comprising:
means for determining MSLV interelectrode conduction delays between detection of events at different LV electrodes from a plurality of LV electrodes of the multi-pole LV lead;
means for setting MSLV interelectrode pacing delays based on the MSLV interelectrode conduction delays for use in delivering MSLV pacing along corresponding pacing vectors using the multi-pole LV lead; and
means for controlling the delivery of MSLV pacing for the corresponding pacing vectors using the MSLV interelectrode pacing delays.

* * * * *